United States Patent [19]

Boyle

[11] Patent Number: 4,625,036
[45] Date of Patent: Nov. 25, 1986

[54] ANTIFUNGAL AZOLE COMPOUNDS

[75] Inventor: Francis T. Boyle, Congleton, United Kingdom

[73] Assignee: Imperial Chemical Industries PLC, London, United Kingdom

[21] Appl. No.: 581,672

[22] Filed: Feb. 21, 1984

[30] Foreign Application Priority Data

Mar. 8, 1983 [GB] United Kingdom ............... 8306351

[51] Int. Cl.$^4$ ............................................. C07D 249/08
[52] U.S. Cl. .......................................... 548/262; 544/132; 546/210; 548/266; 548/269; 548/341
[58] Field of Search ............... 548/262, 341, 266, 269; 424/269, 273 R, 263, 248.56, 248.57, 248.58; 546/210; 544/132

[56] References Cited

U.S. PATENT DOCUMENTS

| | | | |
|---|---|---|---|
| 3,949,080 | 4/1976 | Kramer et al. | 514/383 |
| 4,038,404 | 7/1977 | Meiser et al. | 514/383 |
| 4,358,458 | 11/1982 | Scharwächter et al. | 514/399 |
| 4,404,216 | 9/1983 | Richardson | 548/262 |
| 4,416,682 | 11/1983 | Worthington | 548/262 |
| 4,483,863 | 11/1984 | Richardson et al. | 548/262 X |
| 4,510,148 | 4/1985 | Richardson et al. | 548/262 X |
| 4,554,286 | 11/1985 | Richardson et al. | 548/262 X |
| 4,587,239 | 5/1986 | Regel et al. | 548/262 X |

FOREIGN PATENT DOCUMENTS

| | | | |
|---|---|---|---|
| 0112284 | 6/1984 | European Pat. Off. | 548/341 |
| 0120276 | 10/1984 | European Pat. Off. | 548/262 |
| 3319845 | 12/1984 | Fed. Rep. of Germany | 548/262 |

OTHER PUBLICATIONS

Biochemical Pharmacology, vol. 26, pp. 1039-1042, Pergamon Press, 1977.
"Mode of Action of Antifungal Agents", Symposium of the British Mycological Society, A. P. J. Trinci & J. F. Ryley, Manchester, Sep. 1983, (pp. 321-341).

Primary Examiner—Richard L. Raymond
Attorney, Agent, or Firm—Cushman, Darby & Cushman

[57] ABSTRACT

This invention relates to novel antifungal azole compound of the formula:

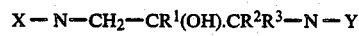
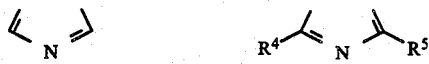

wherein X and Y are CH or N, $R^1$ is optionally substituted phenyl or phenylalkyl, 1-6C alkyl or 3-8C cycloalkyl, $R^2$ and $R^3$ are hydrogen or 1-6C alkyl, and $R^4$ and $R^5$ are hydrogen, $NH_2$, 1-6C alkyl, alkoxyalkyl, aminoalkyl, alkylaminoalkyl, dialkylamino or alkenyl wherein each alkyl, alkoxy or alkenyl part is of 1-6C, phenyl, phenyl-(1-6C)-alkyl, phenoxy-(1-6C)-alkyl or phenyl-(2-6C)-alkenyl in which the phenyl may be optionally substituted, or a heterocyclyl, (heterocyclyl)-(1-6C)-alkyl or (heterocyclyl)-(2-6C)-alkenyl in each of which the heterocyclyl ring may be optionally substituted, provided at least one of $R^2$, $R^3$, $R^4$ and $R^5$ is other than hydrogen, and the acid addition salts of those compounds which contain a basic nitrogen; together with processes for their manufacture; compositions containing them; and a method of combatting plant fungal diseases.

3 Claims, No Drawings

ANTIFUNGAL AZOLE COMPOUNDS

This invention relates to novel antifungal azoles, and in particular it relates to azolyl-propanol derivatives, to a process for preparing them, to pharmaceutical, veterinary and plant antifungal and plant growth regulating compositions containing them, to processes for controlling fungal infections of plants and to processes for regulating plant growth.

European Patent Application No. 81302146.6 discloses azolylpropanol derivatives of the formula:

$$A^1.CH_2.CR(OH).CH_2A^2 \qquad \text{I}$$

wherein R is alkyl, cycloalkyl, aryl or aralkyl, any of which may be optionally substituted, and $A^1$ and $A^2$ are imidazolyl or 1,2,4-triazol-1-yl radicals, and their acid addition salts, metal complexes, ethers and esters, and describes the use of such compounds as pharmaceutical and agricultural antifungals, and as plant growth regulators.

United Kingdom Patent Application No. 2,099,818A describes particularly the compound of the formula I wherein R is a 2,4-difluorophenyl radical, and its pharmaceutical and veterinary antifungal utility.

According to the present invention there is provided a compound of the formula:

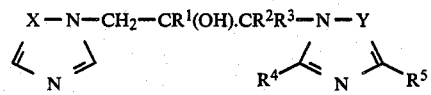

wherein X and Y, which may be the same or different, are each a methylidyne or nitrilo radical, $R^1$ is an optionally-substituted phenyl or phenyl-(1-6C)-alkyl radical, a 1-6C alkyl or a 3-8C cycloalkyl radical, $R^2$ and $R^3$, which may be the same or different, are each hydrogen or a 1-6C alkyl radical, $R^4$ and $R^5$ are each hydrogen, an amino or 1-6C alkyl radical, an alkoxyalkyl, aminoalkyl, alkylaminoalkyl, dialkylaminoalkyl or alkenyl radical, wherein each alkyl, alkoxy or alkenyl part is of 1 to 6 carbon atoms, a phenyl, phenyl-(1-6C)-alkyl, phenoxy-(1-6C)-alkyl or phenyl-(2-6C)-alkenyl radical, in each of which the phenyl ring may be optionally substituted, or a heterocyclyl, (heterocyclyl)-(1-6C)-alkyl or (heterocyclyl)-(2-6C)-alkenyl radical, in each of which the heterocyclyl ring may be optionally substituted, provided that at least one of $R^2$, $R^3$, $R^4$ and $R^5$ is other than hydrogen, and the acid addition salts of those compounds which contain a basic nitrogen.

Preferably, X and Y are each a nitrilo radical, so that the azole rings are each 1,2,4-triazol-1-yl radicals.

A suitable value for $R^1$ when it is a 1-6C alkyl radical is, for example, a methyl, ethyl, propyl, isopropyl, butyl, isobutyl, sec-butyl, tert-butyl, pentyl, neopentyl or hexyl radical.

A suitable value for $R^1$ when it is an cycloalkyl radical is, for example, a cyclopropyl, cyclopentyl or cyclohexyl radical.

A suitable value for $R^2$, $R^3$, $R^4$ or $R^5$, when any of them is a 1-6C alkyl radical, is, for example, any one of those given above for $R^1$, and methyl or ethyl radicals are preferred.

A suitable value for $R^4$ or $R^5$, when either of them is an alkoxyalkyl, aminoalkyl, alkylaminoalkyl, dialkylaminoalkyl or alkenyl radical wherein each alkyl, alkoxy or alkenyl part contains up to 6 carbon atoms, is for example, a methoxymethyl, 6-methoxy-hexyl, hexyloxymethyl, aminomethyl, 6-aminohexyl, methylaminomethyl, 6-methylaminohexyl, hexylaminomethyl, dimethylaminomethyl, 6-dimethylaminohexyl, dihexylaminomethyl, vinyl, allyl, 1-hexenyl or 5-hexenyl radical.

A suitable value for $R^4$ or $R^5$ when either is a phenyl-(1-6C)-alkyl, phenoxy-(1-6C)-alkyl or phenyl-(2-6C)-alkenyl radical is, for example, a benzyl, phenethyl, α-methylphenethyl, 1-phenylethyl, 3-phenylpropyl, phenoxymethyl, styryl, α-methylstyryl or cinnamyl radicals.

Suitable optional substituents in $R^1$ when it is an optionally substituted phenyl or phenyl-(1-6C)-alkyl radical, or in $R^4$ or $R^5$ when either is an optionally-substituted phenyl, phenyl-(1-6C)-alkyl, phenoxy-(1-6C)-alkyl or phenyl-(2-6C)-alkenyl radical is, for example, a halogen atom, for example a fluorine, chlorine, bromine or iodine atom, a 1-6C alkyl, alkoxy or halogenalkyl radical, for example a methyl, propyl, hexyl, methoxy, tert-butoxy, hexyloxy, trichloromethyl, trifluoromethyl, or 2,2,2-trifluoroethyl radical, a 1-6C alkylamino or di(1-6C alkyl)amino radical, for example a methylamino, hexylamino, dimethylamino or diethylamino radical, a 1-6C alkylsulphonyl radical, for example a mesyl radical, or a heterocyclyl-(1-6C)alkyl radical, for example a morpholinoalkyl, piperidinoalkyl, 1-pyrrolidinylalkyl, 4-(1-6C alkyl)piperazinylalkyl or 4-(2-6C alkanoyl)piperazinylalkyl radical. Up to five such optional substituents may be present, but mono- and disubstituted such radicals are preferred.

A suitable value for $R^4$ and $R^5$ when either is a heterocyclyl radical, or for the heterocyclyl part of $R^4$ or $R^5$ when either is a (heterocyclyl)alkyl or (heterocyclyl)alkenyl radical, is, for example a nitrogen-containing heterocyclyl radical, for example a pyridyl, pyrimidinyl, pyrazinyl, piperidino or morpholino radical. Particular such radicals are thus, for example, a pyridyl, pyridylmethyl, 2-(2-pyridyl)vinyl, piperidinomethyl or morpholinomethyl radical.

Suitable optional substituents in such heterocyclyl, (heterocyclyl)alkyl or (heterocyclyl)alkenyl radicals are those given above for optional substituents in $R^1$.

It will be understood that, since the carbon atom bearing substituents $R^1$ and hydroxy is asymmetrically substituted, and the carbon atom bearing substituents $R^2$ and $R^3$ may also be asymmetrically substituted, the compounds of the invention will exist in racemic, meso or optically-active forms. It is common general knowledge in the art how such forms may be separated and isolated, and their antifungal properties determined.

Suitable acid addition salts of compounds of the formula II which contain a basic nitrogen are, for example, the hydrochloride, nitrate, sulphate, acetate, toluene-p-sulphonate or maleate.

A preferred group of compounds of the invention comprises compounds of the formula II wherein $R^4$ is hydrogen and $R^5$ is a substituent, other than hydrogen, as defined above.

A further preferred group of compounds of the invention comprises compounds of the formula II wherein X and Y are each a nitrilo radical, $R^2$, $R^3$ and $R^4$ are each a hydrogen atom, $R^1$ is a phenyl radical which bears one or two substituents selected from trifluoromethyl and halogen, especially fluorine and chlorine, and particularly fluorine, and $R^5$ is a phenyl or styryl radical similarly substituted.

A particularly preferred sub-group within the above preferred group comprises those compounds wherein $R^1$ is a 4-trifluoromethyl-, 2,4-difluoro-, 2,4-dichloro- or 2-fluoro-4-trifluoromethyl-phenyl radical, and $R^5$ is a 4-trifluoromethyl-, 4-fluoro-, 2,4-difluoro- or 4-chlorophenyl or -styryl radical.

A further preferred group of compounds of the invention comprises compounds of the formula II wherein X and Y are each a nitrilo radical, $R^2$, $R^4$ and $R^5$ are each a hydrogen atom, $R^3$ is a methyl radical, and $R^1$ is a phenyl radical bearing one or two substituents selected from trifluoromethyl and halogen, especially fluorine or chlorine, and particularly fluorine. Particular preferred values for $R^1$ in this group are the 4-fluorophenyl, 4-chlorophenyl, 4-trifluoromethylphenyl, 2,4-difluorophenyl and 2-fluoro-4-trifluoromethylphenyl radicals.

A further preferred group of compounds of the invention comprises compounds of the formula II wherein X and Y are each a nitrilo radical, $R^2$ and $R^3$ are each a methyl radical, $R^4$ and $R^5$ are each a hydrogen atom, and $R^1$ is a phenyl radical bearing one or two substituents selected from trifluoromethyl and halogen, especially fluorine or chlorine, and particularly fluorine. Particular preferred values for $R^1$ in this group are the 4-chlorophenyl, 4-trifluoromethylphenyl, 2,4-difluorophenyl and 2-fluoro-4-trifluoromethylphenyl radicals.

Particularly preferred compounds of the invention are those wherein X and Y are each a nitrilo radical, $R^2$, $R^3$ and $R^4$ are each a hydrogen atom, $R^1$ is a 4-trifluoromethylphenyl or 2,4-difluorophenyl radical and $R^5$ is a 4-trifluoromethylphenyl, 4-trifluoromethylstyryl, 4-fluorophenyl, 4-fluorostyryl, 2,4-difluorophenyl or 2,4-difluorostyryl radical.

The compounds of the formula II may be prepared by methods known generally for the manufacture of similar compounds. Thus, the following processes are provided as further features of this invention, wherein X, Y, $R^1$, $R^2$, $R^3$, $R^4$ and $R^5$ have the meanings defined above.

(a) the reaction of an epoxide of the formula:

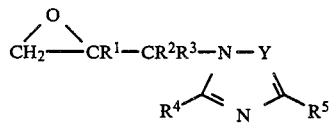   III either as such, or formed in situ, with an azole of the formula:

   IV in the presence of a strong base; or (b) the reaction of an epoxide of the formula:

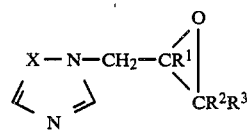   V either as such, or formed in situ, with an azole of the formula:

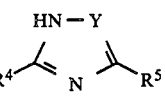   VI in the presence of a strong base; or (c) the reaction of a halogeno compound of the formula:

$$ZCH_2.CR^1(OH)CR^2R^3Z \quad \text{or} \quad \text{VIIA}$$

   VIIB wherein Z is a halogen, preferably bromine or iodine, with an azole of the formula VI; or (d) the reaction of a halogeno compound of the formula:

$$ZCH_2.CR^1(OH).CR^2R^3{-}N{-}Y$$

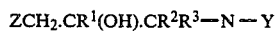   VIII wherein Z has the meaning stated above, with an azole of the formula IV.

(e) the reaction of a ketone of the formula:

$$X{-}N{-}CH_2.CO.CR^2R^3{-}N{-}Y$$

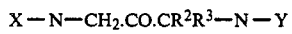   IX with a Grignard reagent, $R^1MgHal$, wherein Hal is a halogen, or when $R^1$ is an aryl radical, with an aryl lithium derivative, $R^1Li$;

(f) the reaction of a ketone of the formula:

$$R^1CO.CR^2R^3{-}N{-}Y \qquad X{-}N{-}CH_2.COR^1$$

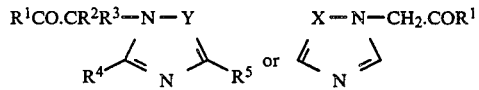

X  XI with a Wittig reagent of the formula:

$$X{-}N{-}CH_2{-}Q \quad \text{or} \quad Q{-}CR^2R^3{-}N{-}Y$$

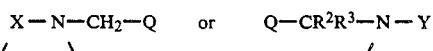

XII  XIII respectively, wherein Q is a triphenylphosphine halide $(Hal^-.Ph_3P_6{^+}{-})$ or trialkyl phosphite $(R^6O)_2PO{-}$, (wherein $R^6$ is 1-6C lower alkyl) radical, which Wittig reagent may be preformed or formed in situ.

The epoxide of the formula III, wherein Y is nitrilo, used as starting material in the above process, may be obtained by reacting a nitrile $R^7CN$ (XIV) wherein $R^7$ has any of the meanings given above for $R^4$ or $R^5$, other than hydrogen, with for example ethanol in the presence of an acid to form an imido-ester XV, which is then reacted with formohydrazide, NH₂.NH.CHO, to form a triazole XVI. The triazole XVI is then reacted with an α-bromoketone XVII, obtained by bromination of a ketone XVIII, to form a mixture of azolyl ketones X (one of R⁴ and R⁵=R⁷, the other=hydrogen) which on reaction with dimethyl sulphonium methylide or dimethyl oxosulphonium methylide provides a triazole epoxide starting material of the formula III.

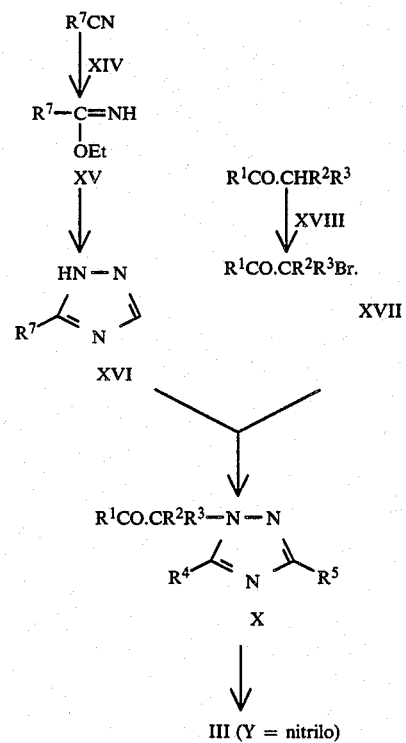

The epoxide of the formula III, wherein Y is methylidyne, may be prepared by the reaction of a Grignard reagent, R⁵MgI, with ethyl cyanoacetate (XIX) to form a β-keto-ester XX. The β-keto-ester XX is reacted with sodium nitrite to form the oxime XXI which is reduced to the corresponding amine XXII, and this amine is cyclised with an amide, R⁴CONH₂, to form a substituted imidazole ester XXIII². This ester XXIII is then hydrolysed and decarboxylated to produce a substituted imidazole, XXIV, which is used in place of the triazole XVI in the reaction sequence described above, to form the epoxide III (Y=methylidyne).

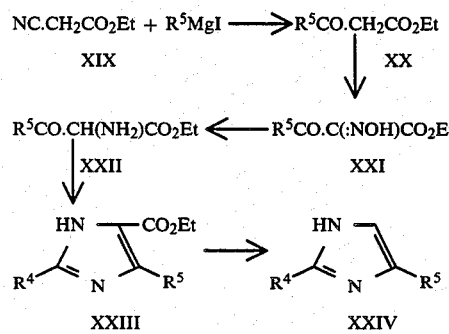

Alternatively, an epoxide III wherein Y is methylidyne and R⁴ is hydrogen may be manufactured by reacting methyl isocyanoacetate (XXV) with a nitrile, R⁵CN, to form an imidazole ester (XXVI), which is then hydrolysed and decarboxylated, and the imidazole so obtained (XXVII) is used in place of the triazole XVI in the reaction sequence described above, in order to obtain an epoxide III wherein Y is methylidyne and R⁴ is hydrogen.

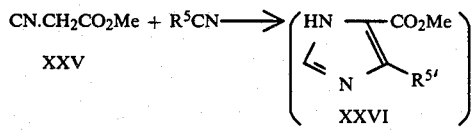

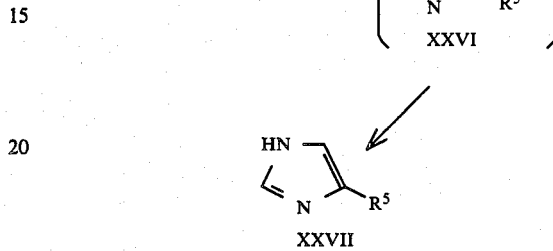

The epoxide of the formula V, used as starting material in the above process, may be obtained by brominating a methyl ketone XXVIII, treating the bromoketone XXIX thus obtained with imidazole or 1,2,4-triazole in the presence of a strong base to form the triazole ketone XXX, and reacting the triazole ketone XXX with Wittig reagent of the formula XXXI, wherein Q has the meaning stated above. The olefin XXXII thus obtained is then epoxidised, for example with m-chloroperbenzoic acid, to form the required epoxide starting material V.

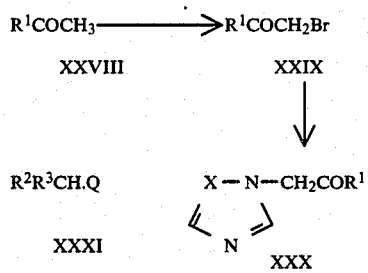

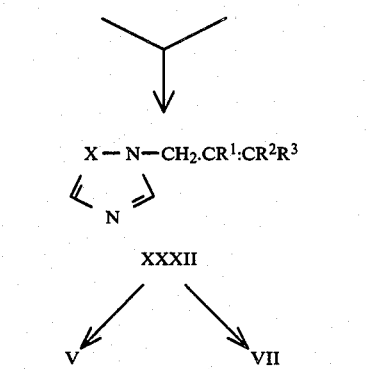

Alternatively, the epoxide III or the epoxide V, when R² and R³ are both hydrogen, may be formed in situ in the reaction from the corresponding ketone and dimethylsulphonium iodide or dimethylsulphoxonium iodide.

The halogeno compound of the formula VII, used as starting material in the above process, may be obtained by reacting an olefin XXXII with a hypohalous acid in conventional manner.

The halogeno compound of the formula VIII, used as starting material in the above process, may be obtained in a similar manner to VII, using an appropriate ketone in place of the methyl ketone XXVIII, and reacting the bromoketone corresponding to XXIX with an appropriate substituted azole in place of imidazole or 1,2,4-triazole.

The ketones of the formula IX and XI, used as starting materials in the above process, may be manufactured by the same general process as described above for the manufacture of the ketone X.

The Wittig reagents of the formulae XII and XIII, used as starting materials in the above process, may be manufactured by reacting 1-chloromethyl-1,2,4-triazole with either triphenylphosphine, as described in European Patent Publication No. 60222, or with potassium diethyl phosphite.

As indicated above, the compounds of the invention possess antifungal properties which make them useful in the treatment of candidosis and human dermatophyte infections.

This antifungal activity against *Candida albicans*, a causative fungus of candidosis, and *Trichophyton mentagrophytes*, var. *quinkeanum*, a causative fungus of ringworm, was demonstrated as follows:

Female mice of around 30 g. weight are injected sub-cutaneously on a Friday with 0.5 mg. of oestradiol benzoate. The following Monday (day 0) they are clipped on the back and then dosed orally with test compounds. They are then inoculated with *Candida albicans* in the vagina and *Trichophyton mentagrophytes* var. *quinkeanum* on the back, and then given a second dose of the same compound. Dosing is repeated once daily on days 1–4. On day 7 skin lesions are scored visually and vaginal samples taken for culture on agar. Groups of 5 mice are used and compounds are dosed initially at a level of 250 mg./kg. The dose is then reduced sequentially until a minimum effective dose (MED) is found. For example, the MED for 1-(2,4-dichlorophenyl)-2-[5-(4-chlorostyryl)-1,2,4-triazol-1-yl]-1-(1,2,4-triazol-1-ylmethyl)ethanol in this test was 5 mg. per kg., and no overt toxicity was seen at this MED.

Thus, according to a further feature of the invention there is provided a pharmaceutical or veterinary antifungal composition which comprises an antifungally effective amount of compound of the formula II together with a pharmaceutically or veterinarily acceptable diluent or carrier.

The composition of the invention may be in a conventional pharmaceutical form suitable for oral administration, for example a tablet, a capsule, an emulsion or an aqueous or oily solution or suspension, or suitable for topical application, for example a cream, ointment or gel. The composition may contain conventional pharmaceutical excipients, and may be manufactured by conventional pharmaceutical techniques.

Preferred pharmaceutical or veterinary compositions of the invention are compositions suitable for oral administration, and particularly tablets and capsules containing from 1 to 100, preferably 5 to 50 mg. of a compound of the invention.

The compounds of the invention also possess antifungal properties which are useful in combatting a wide variety of plant fungal diseases.

The compounds can move acropetally when applied to the plant tissue, and can also be volatile enough to be active in the vapour phase against fungi on the plant.

The compounds may be used as such for plant fungicidal purposes but are more conveniently formulated into compositions for such usage. The invention thus provides also a plant fungicidal composition comprising a compound of general formula II and a non-pharmaceutical carrier or diluent.

The invention also provide a method of combatting fungal diseases in a plant, which method comprising applying to the plant, to seed of the plant or to the locus of the plant or seed a compound of the formula II.

The compound can be applied in a number of ways, for example it can be applied, formulated or unformulated, directly to the foliage of a plant, to seeds or to the medium in which plants are growing or are to be planted, or it can be sprayed on, dusted on or applied as a cream or paste formulation, or it can be applied as a vapour. Application can be to any part of the plant, bush or tree, for example to the foliage, stems, branches or roots, or to soil surrounding the roots, or to the seed before it is planted.

The term "plant" as used herein includes seedlings, bushes and trees. Furthermore, the fungicidal method of the invention includes preventative, protectant, prophylactic and eradicant treatment.

The compounds are preferably used for agricultural and horticultural purposes in the form of a composition. The type of composition used in any instance will depend upon the particular purpose envisaged, and the choise of a suitable conventional composition, and the method by which such a composition may be manufactured, are apparent to those skilled in the art.

The plant fungicidal compositions of this invention can comprise also other compound(s) having biological activity, e.g. compounds having similar or complementary fungicidal activity or compounds having plant growth regulating, herbicidal or insecticidal activity.

The invention is illustrated, but not limited, by the following Examples, in which temperatures are given in degrees Celsius.

EXAMPLE 1

A mixture of 2,4-dichloro-α-(1,2,4-triazol-1-yl)acetophenone (1.5 g), trimethylsulphoxonium iodide (1.6 g.), 3-(4-chlorostyryl)-1,2,4-triazole (1.4 g.) and potassium hydroxide (0.8 g.) in tert-butyl alcohol (15 ml.) was stirred and heated at 70° for 16 hours. The reaction mixture was evaporated to dryness and the residual gum was partitioned between ethyl acetate and water. The ethyl acetate layer was separated, washed with water, dried with anhydrous magnesium sulphate and filtered, and the filtrate was evaporated to dryness. The residual gum was subjected to medium pressure liquid chromatography (MPLC) on K60 silica using chloroform/petroleum ether (b.p. 60°–80°) 75/25, v/v, then chloroform and then methanol/chloroform 2/98 v/v, as eluting solvents to give 1-(2,4-dichlorophenyl)-2-[3-(4-chlorostyryl)-1,2,4-triazol-1-yl]-1-(1,2,4-triazol-1-ylmethyl)ethanol, m.p. 155°–7° and 1-(2,4-dichlorophenyl)-2-[5-(4-chlorostyryl)-1,2,4-triazol-1-yl]-1-(1,2,4-triazol-1-ylmethyl)ethanol m.p. 193°–6°.

The 3-(4-chlorostyryl)-1,2,4-triazole used as starting material in the above example may be prepared as follows:

4-Chlorocinnamonitrile (5 g.) was dissolved in a mixture of diethyl ether (10 ml.) and absolute ethanol (5 ml.) and stirred at 0°. Hydrogen chloride gas was passed into the solution for 1 hour and the resulting solution was allowed to stand at 5° for 16 hours.

The resulting white crystals were filtered and washed with ether to give a white solid which was redissolved in ethanol (50 ml.). This solution was treated successively with triethylamine (5 ml.) and a solution of formohydrazide (2 g.) in ethanol (15 ml.) and stirred at room temperature for 2 hours. The resulting solution was heated under reflux for 1 hour, then evaporated to dryness. The residue was partitioned between ethyl acetate and water, the ethyl acetate layer was then dried with anhydrous magnesium sulphate and filtered, and the filtrate was evaporated to dryness. The residual gum was subjected to medium pressure chromatography on K60 silica, using chloroform as the eluting solvent, to give 3-(4-chlorostyryl)-1,2,4-triazole, m.p. 178°–182°.

The 2,4-dichlorophenyl-α-(1,2,4-triazole-1-yl)acetophenone used as the starting material in the above process may be prepared as follows:

α,2,4-Trichloroacetophenone (20 g.) was dissolved in acetonitrile (25 ml.) and added dropwise to a refluxing solution of 1,2,4-triazole (6.2 g.) and potassium carbonate (13.4 g.) in acetonitrile (25 ml.). When the addition was complete, the solution was allowed to cool and was stirred for 2 hours. The solvent was evaporated and the residue was partitioned between ethyl acetate and water. The ethyl acetate layer was separated, washed twice with water and twice with brine, dried over sodium sulphate and filtered. The filtrate was evaporated to dryness under reduced pressure, and the residue was chromatographed on a K60 silica column, eluting with ethyl acetate, to give 2,4-dichloro-α-(1,2,4-triazol-1-yl)-acetophenone, which after crystallisation from ethyl acetate/petroleum ether (b.p. 60°–80°), had m.p. 116°–117°.

EXAMPLES 2–13

The process described in the first part of Example 1 was repeated, using the appropriate substituted triazole in place of 3-(4-chlorostyryl)-1,2,4-triazole, to give the following compounds:

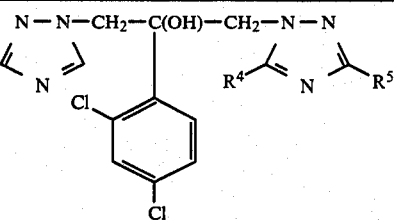

| No. | R⁴ | R⁵ | M.p. |
|---|---|---|---|
| 2 | methyl | H | 166–169 |
| 3 | H | isobutyl | 175–176 |
| 4 | H | 3-phenylpropyl | 102–105 |
| 5 | H | α-methylstyryl | 149–151 |
| 6 | α-methylstyryl | H | 185–187 |
| 7 | H | α-methylphenethyl | 110–113 |
| 8 | H | phenyl | 152–155 |
| 9 | piperidinomethyl | H | 181–183 |
| 10 | 3-trifluoromethylstyryl | H | 193–196 |
| 11 | H | 3-trifluoromethylstyryl | 136–139 |
| 12 | H | 4-fluoro-α-methylstyryl | 119–122 |
| 13 | H | 3-pyridyl | 176–179 |

The substituted triazoles used as starting materials in the preparation of the compounds of Examples 8, 10, 11 and 12 are manufactured by the process described in the second part of Example 1, using the appropriate nitrile in place of 4-chlorocinnamonitrile:

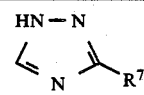

| Triazole for Example No. | R¹ | M.p. |
|---|---|---|
| 8 | phenyl | 100–104 |
| 10 and 11 | 3-trifluoromethylstyryl | 134–138 |
| 12 | 4-fluoro-α-methylstyryl | 97–101 |

The 3-(3-pyridyl)-1,2,4-triazole used as starting material for Example 13 was prepared by a modification of this synthesis, as follows:

3-Cyanopyridine (20.8 g.) was dissolved in methanol (50 ml.) and treated with a solution of sodium (0.5 g.) in methanol (15 ml.). After standing for 48 hours at room temperature, a solution of formohydrazide (12 g.) in ethanol (50 ml.) was added and the mixture was stirred at room temperature for two hours, then heated under reflux for one hour. The product was evaporated to dryness and the residue was dissolved in the minimum of water and extracted three times with ethyl acetate (100 ml.). The organic extracts were combined, dried with anhydrous magnesium sulphate, filtered and evaporated to dryness. The residue was boiled with ethyl acetate (50 ml.), cooled and filtered to give 3-(pyrid-3-yl)-1,2,4-triazole m.p. 165°–8°.

The 3-isobutyl-1,2,4-triazole used as starting material for Example 3 was prepared as follows:

Isovaleryl chloride (100 g.) was added dropwise over 45 minutes to a stirred solution of thiosemicarbazide (75 g.) in dry pyridine (800 ml.) at −5° to 0°. When the addition was complete the solution was stirred overnight at room temperature, then the solvent was evaporated under reduced pressure and the residue was dissolved in absolute ethanol (500 ml.). This solution was added to a solution of sodium (39 g.) in absolute ethanol (500 ml.), heated under reflux overnight, cooled and filtered, and the solvent was evaporated under reduced pressure. The residue was dissolved in water (250 ml.) and acidified with concentrated hydrochloric acid (about 150 ml.) to precipitate 5-isobutyl-1,2,4-triazol-2- thiol, which was filtered off, washed with water and air-dried, m.p. 167°–169°.

This thiol was added in portions to a stirred solution of concentrated nitric acid (180 ml.) in water (480 ml.) at a temperature of 40°–60°. After the addition was complete, the mixture was stirred for 16 hours at room temperature, neutralized to pH 7 with 12N sodium hydroxide solution, and extracted twice with dichloromethane. The organic extracts were combined, dried, and evaporated to dryness under reduced pressure to give 3-isobutyl-1,2,4-triazole, m.p. 71°–73°.

The substituted triazoles used as starting materials for Examples 4, 5, 6 and 7 were obtained similarly:

HN—N
$\diagdown_N\diagup^{R^7}$

| Triazole for Example No. | R$^7$ | M.p. |
|---|---|---|
| 4 | 3-phenylpropyl | 40–42 |
| 5 and 6 | α-methylstyryl | 94–96 |
| 7 | α-methylphenethyl | 104–106 |

The 3-piperidinomethyl-1,2,4-triazole used as starting material for Example 9 was prepared as follows:

3-Chloromethyl-1,2,4-triazole hydrochloride (0.5 g.) was added to piperidine (10 ml.) and the mixture was heated at 100° for 16 hours, then evaporated to dryness. The residue was dissolved in water (10 ml.) and basified with sodium bicarbonate. The resulting solution was evaporated to dryness and the residue was extracted twice with ethanol (50 ml.). The combined extracts were evaporated to dryness and the residual gum was subjected to MPLC on K60 silica gel using methanol/chloroform, 3/97 v/v, as solvent to give 3-(piperidinomethyl)-1,2,4-triazole with NMR data as follows: solvent—CDCl$_3$: 8.05 ppm (singlet, 1H), 3.75 ppm (singlet, 2H), 2.5 ppm (multiplet, 4H) and 1.6 ppm (multiplet, 6H).

EXAMPLE 14

4-Chloro-α-(3-isopropyl-1,2,4-triazol-1-yl)-propiophenone (2.91 g.), trimethylsulphoxonium iodide (2.5 g.), potassium hydroxide (1.5 g.) and 1,2,4-triazole (0.83 g.) were dissolved in tert-butyl alcohol (25 ml.) and heated under reflux for 3 hours. The reaction mixture was cooled, poured into water and extracted with ethyl acetate. The ethyl acetate layer was separated, washed with brine and dried, and the solvent was evaporated under reduced pressure. The residue was purified by MPLC on K60 silica eluting with ethyl acetate/petroleum ether (b.p. 60°–80°), 1:1 v/v, to give 1-(4-chlorophenyl)-2-(3-isobutyl-1,2,4-triazol-1-yl)-1-(1,2,4-triazol-ylmethyl)-propanol, m.p. 140°–141°.

The 4-chloro-α-(3-isobutyl-1,2,4-triazol-1-yl)-propiophenone used as starting material in the above process may be prepared as follows:

4-Chloropropiophenone (33.6 g.) was dissolved in anhydrous diethyl ether (50 ml.), stirred and cooled in an ice bath while bromine (32 g.) was added dropwise over 30 minutes. The solid which formed was filtered off, washed with water and air-dried to give 2-bromo-4'-chloropropiophenone, m.p. 77°–79°.

Sodium hydride (50% dispersion in oil, 2.6 g.) was washed twice with petroleum ether (b.p. 40°–60°) then suspended in dimethylformamide (75 ml.). The suspension was stirred while 3-isobutyl-1,2,4-triazole (6.3 g.) was added dropwise. When effervescence ceased, the mixture was stirred for 30 minutes at room temperature, then 2-bromo-4'-chloropropiophenone (12.4 g.) was added, and the solution was heated at 70° for 2 hours. The reaction mixture was cooled, poured into water and extracted with ethyl acetate. The extract was washed with brine and dried, the solvent was evaporated under reduced pressure, and the residue was purified by MPLC on silica, eluting with a mixture of ethyl acetate and petroleum ether (b.p. 40°–60°), 1:4 v/v, to give the required starting material, 4-chloro-α-(3-isobutyl-1,2,4-triazol-1-yl)propiophenone as a yellow oil.

EXAMPLES 15–17

The process described in the first part of Example 14 was repeated, using the appropriate 2-(1,2,4-triazol-1-yl)propiophenone as starting material to give:

15. 1-(4-chlorophenyl)-2-(1,2,4-triazol-1-yl)-1-(1,2,4-triazol-1-ylmethyl)propanol, m.p. 103°–105°
16. 2-(1,2,4-triazol-1-yl)-1-(1,2,4-triazol-1-ylmethyl)-1-(4-trifluoromethylphenyl)propanol, m.p. 120°–122°
17. 1-(4-fluorophenyl)-2-(1,2,4-triazol-1-yl)-1-(1,2,4-triazol-1-ylmethyl)propanol, m.p. 109°–110°.

The appropriate 2-(1,2,4-triazol-1-yl)propiophenones used as starting materials for the preparation of these compounds were manufactured by processes entirely analogous to those described in the second part of Example 14.

N—N—CH(CH$_3$)—COR$^1$
$\diagdown_N\diagup$

| Triazole for Example No. | R$^1$ | M.p. |
|---|---|---|
| 15 | 4-chlorophenyl | 79–80 |
| 16 | 4-trifluoromethylphenyl | oil |
| 17 | 4-fluorophenyl | oil |

EXAMPLES 18–54

The process described in the first part of Example 1 was repeated, using the appropriate substituted triazole in place of 3-(4-chlorostyryl)-1,2,4-triazole, to give the compounds shown in the following Table:

N—N—CH$_2$—C(OH)—CH$_2$—N—N

| No. | R$^9$ | R$^8$ | R$^4$ | R$^5$ | M.p. |
|---|---|---|---|---|---|
| 18 | Cl | Cl | morpholinomethyl | H | 148–151 |
| 19 | Cl | Cl | H | NH$_2$ | 166–172 |
|    | Cl | Cl | NH$_2$ | H | (a) |
| 20 | Cl | H | NH$_2$ | H | 182–184 |
| 21 | Cl | Cl | α-methyl-4-fluorostyryl | H | 147–150 |
| 22 | Cl | Cl | H | 4-chlorophenoxymethyl | 122–126 |
| 23 | Cl | Cl | 4-chlorophenoxymethyl | H | 177–180 |
| 24 | Cl | H | H | 4-chlorophenyl | 151–154 |

-continued $$\text{N=N-CH}_2\text{-C(OH)-CH}_2\text{-N=N}$$

structure with R⁸, R⁹, R⁴, R⁵ substituents on triazole-phenyl-triazole

| No. | R⁹ | R⁸ | R⁴ | R⁵ | M.p. |
|---|---|---|---|---|---|
| 25 | Cl | H | H | 4-chlorophenyl | 165–170 |
| 26 | Cl | H | H | 4-mesylphenoxymethyl | 150–152 |
| 27 | Cl | H | H | 4-fluorobenzyl | 128–131 |
| 28 | Cl | H | 4-fluorobenzyl | H | 172–175 |
| 29 | Cl | H | H | α-methyl-4-mesylstyryl | 115–119 |
| 30 | Cl | H | H | 4-fluorostyryl | 177–180 |
| 31 | Cl | H | H | 2,4-dichlorostyryl | 190–200 |
| 32 | Cl | H | 2,4-dichlorostyryl | H | 190–194 |
| 33 | F | F | H | 4-trifluoromethylphenyl | 163–166 |
| 34 | F | F | H | 4-fluorostyryl | 142–145 |
| 35 | F | F | 4-fluorostyryl | H | 126–129 |
| 36 | F | F | H | 4-trifluoromethylstyryl | 104–107 |
| 37 | Cl | Cl | H | styryl | 78–85 |
|  | Cl | Cl | styryl | H | (b) |
| 38 | CF₃ | H | H | 4-fluoro-α-methylstyryl | 69–70 |
| 39 | CF₃ | H | 4-fluoro-α-methylstyryl | H | 144–145 |
| 40 | CF₃ | H | H | 4-fluorophenyl | 128–130 |
| 41 | CF₃ | H | H | 4-chlorophenyl | 133–135 |
| 42 | F | F | H | 4-chlorostyryl | 105–107 |
| 43 | F | F | 4-chlorostyryl | H | 155–157 |
| 44 | F | F | H | 4-methoxystyryl | 150–152 |
| 45 | CF₃ | H | H | 4-methoxyphenyl | 181–183 |
| 46 | F | F | H | 4-fluorophenyl | 165–167 |
| 47 | CF₃ | H | H | 4-fluorostyryl | 234–236 |
| 48 | CF₃ | H | H | 3,4-difluorophenyl | 134–136 |
| 49 | F | F | H | 2,4-difluorophenyl | 144–147 |
| 50 | F | F | H | 2,4-dichlorostyryl | 181–183 |
| 51 | Cl | H | 4-fluorobenzoyl | H | 100(dec)* |
| 52 | F | F | H | 3-pyridyl | 154–155 |
| 53 | F | F | H | 5-trifluoromethyl-2-pyridyl | 152–153 |
| 54 | CF₃ | H | H | 4-pyridyl | 189–190 |
| 55 | CF₃ | H | H | 4-trifluoromethylphenyl | 182–184 |
| 56 | F | F | H | 1-propenyl | 159–161 |

(a)-a 1:1 mixture of the 2 isomers
(b)-a 4:1 mixture of the 2 isomers
*decomposition.

The following substituented triazoles used as starting materials in the preparation of the compounds of Examples 22–37, 40, 41 and 44–50 were manufactured by the process described in the second part of Example 1, using the appropriate nitrile in place of 4-chlorocinnamonitrile, but allowing the hydrogen chloride gassed solution to stand at 5° for 48 instead of 16 hours, and heating the residual gum at 120° for 1 hour prior to medium pressure chromatography:

$$\text{HN-N} \overset{}{\underset{N}{\diagdown}} R^7$$

| Triazole for Example No. | R⁷ | M.p. |
|---|---|---|
| 22, 23 | 4-chlorophenoxymethyl | 139–143 |
| 24, 25, 41 | 4-chlorophenyl | 185–189 |
| 26 | 4-mesylphenoxymethyl | 188–192 |
| 27, 28 | 4-fluorobenzyl | 92–95 |
| 29 | α-methyl-4-mesylstyryl | 165–168 |
| 30, 34, 35, 47 | 4-fluorostyryl | 140–143 |
| 36 | 4-trifluoromethylstyryl | 141–143 |
| 40, 46 | 4-fluorophenyl | 163–164 |
| 37 | styryl | 98–101 |
| 44 | 4-methoxystyryl | 144–146 |
| 45 | 4-methoxyphenyl | 110–112 |
| 48 | 3,4-difluorophenyl | 147–148 |
| 49 | 2,4-difluorophenyl | 131–132 |
| 31, 32, 50 | 2,4-dichlorostyryl | 211–213 |
| 33, 55 | 4-trifluoromethylphenyl | 182–184 |
| 56 | 1-propenyl | 90–95 |

The following substituted triazoles used as starting materials in the preparation of the compounds of Examples 43 and 54 respectively were manufactured by the process described in the second part of Examples 2–13 for the manufacture of 3-(3-pyridyl)-1,2,4-triazole, using the appropriate cyanopyridine in place of 3-cyanopyridine:

3-(5-trifluoromethyl-2-pyridyl)-1,2,4-triazole, m.p. 183–185.

3-(4-pyridyl)-1,2,4-triazole, m.p. 213–215.

The process described at the end of Examples 2–13 for the preparation of 3-piperidinomethyl-1,2,4-triazole was repeated, using morpholine in place of piperidine, to manufacture 3-morpholinomethyl-1,2,4-triazole, which is used as starting material in the manufacture of the compound of Example 18 (NMR in deuteriochloroform: 8:2 ppm (singlet, 1H), 3.8 (complex, 6H), 2.6 (complex, 4H)).

The compound 3-(4-fluorobenzoyl)-1,2,4-triazole used as starting material for the manufacture of the compound of Example 51 was prepared as follows:

3-(4-Fluorobenzyl)-1,2,4-triazole (9 g.) and potassium permanganate (13.5 g.) were heated in water at 80° for 1 hour. The reaction mixture was filtered, and the residue was washed twice each with water and chloroform. The combined filtrate and washings were adjusted to pH 3 and filtered. The solid residue was dissolved, as far as possible, in hot methanol, the solution was filtered and evaporated to dryness to give 3-(4-fluorobenzoyl)-1,2,4-triazole as a cream-colored solid, m.p. 225°–230°.

The process described in the third part of Example 1 was repeated, using the appropriate acetophenone in place of α,2,4-trichloroacetophenone, to manufacture the following triazole-acetophenones for use as starting materials in the preparation of the compounds of Examples 20, 24–31, 33–36, 38–54:

$$R^9\text{-}\underset{R^8}{\text{C}_6\text{H}_3}\text{-COCH}_2\text{N}\diagdown\text{triazole}$$

| Triazole acetophenone for Examples No. | R⁸ | R⁹ | M.p. |
|---|---|---|---|
| 20,24–31,45,51 | H | Cl | 151–152 (a) |
| 33–36,42–44,46,49,50, | F | F | 106–109 (b) |

-continued

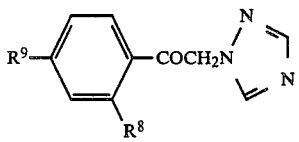

| Triazole acetophenone for Examples No. | R⁸ | R⁹ | M.p. |
|---|---|---|---|
| 52,53 | | | |
| 38–41,45,47,48,54 | H | CF₃ | 126–129 (c) |

(a) Sodium hydride used in place of potassium carbonate.
(b) Reaction refluxed for 45 min. after mixing of reagents then worked up immediately.
(c) Reagents mixed at 0°, stirred at 0° for 2 hours, then at room temperature for 2 hours.

EXAMPLE 56

2-(2-Fluoro-4-trifluoromethylphenyl)-2-(1,2,4-triazole-1-ylmethyl)oxirane (0.4 g.) and 3-(4-fluorophenyl)-1,2,4-triazole (0.3 g.) were added to a solution of sodium hydride (0.1 g. of a 50% dispersion in oil) in tert-butyl alcohol (10 ml.) and the mixture was heated at 80° for 16 hours. The reaction mixture was evaporated to dryness and the residual gum was partitioned between ethyl acetate and water. The organic layer was separated, dried and evaporated to dryness. The residual gum was chromatographed on a K60 silica column, eluting successively with chloroform/petroleum ether (b.p. 60°–80° C.) 60/40 v/v, 70/30 v/v and 80/20 v/v, to give 2-[3-(4-fluorophenyl)-1,2,4-triazole-1-yl]-1-(2-fluoro-4-trifluoromethylphenyl)-1-(1,2,4-triazole-1-ylmethyl)-ethanol, m.p. 96°–100°.

The 2-(2-fluoro-4-trifluoromethylphenyl)-2-(1,2,4-triazol-1-ylmethyl)oxirane used as starting material in the above example may be prepared as follows:

1,3-Dichloro-2-(2-fluoro-4-trifluoromethylphenyl)-2-propanol (7 g.) was added to a solution of sodium hydride (1.45 g. of 48% dispersion in oil) in tert-butyl alcohol (30 ml.) and heated at 100° C. for 1 hour. The mixture was evaporated to dryness and the residue was partitioned between ethyl acetate and water. The organic layer was separated, washed with water and dried with anhydrous magnesium sulphate, and the filtered solution was evaporated to dryness to give 2-chloromethyl-2-(2-fluoro-4-trifluoromethylphenyl)oxirane as a yellow oil.

A solution of 2-chloromethyl-2-(2-fluoro-4-trifluoromethylphenyl)oxirane (6 g.) in tert-butyl alcohol was treated with sodium 1,2,4-triazole (2.7 g.) and heated at 100° for 1 hour. The mixture was evaporated and the residual gum partitioned between ethyl acetate and water. the organic layer was washed with water, dried and evaporated to dryness. The residual gum was chromatographed on K60 silica gel using chloroform/petroleum ether (b.p. 60°–80°) 1:1 v/v and chloroform as eluting solvents to give 2-(2-fluoro-4-trifluoromethylphenyl)-2-(1,2,4-triazol-1-ylmethyl)oxirane, as a gum with NMR data as follows:

Solvent CDCl₃: 8.1 ppm (singlet-1H), 7.9 ppm (singlet-1H) 7.3 ppm (complex-3H), 4.9 ppm (doublet-1H), 4.5 ppm (doublet-1H), 2.9 ppm (quartet-2H).

EXAMPLE 57

2-Bromo-1-bromomethyl-1-(2-fluoro-4-trifluoromethylphenyl)propanol (30 g.), sodium 1,2,4-triazole (20.6 g.) and dimethylformamide (175 ml.) were heated together on a steam bath for 3 days. The reaction mixture was cooled and poured into water, and extracted twice with ethyl acetate. The combined extracts were washed twice with water, then with brine, and were dried, filtered and evaporated to dryness. The residue was chromatographed on silica. Elution with 50% v/v ethyl acetate/petroleum ether (b.p. 60°–80° C.) gave a mixture of diastereoisomers, which was re-chromatographed on LOBAR (trade mark) silica. Elution with 20% v/v absolute ethanol in hexane gave the less polar epimer, m.p. 174°–175° after crystallisation from ethyl acetate/hexane, and the more polar epimer, m.p. 187°–189°, after crystallisation from ethyl acetate/hexane, of 1-(2-fluoro-4-trifluoromethylphenyl)-2-(1,2,4-triazol-1-yl)-1-(1,2,4-triazol-1-ylmethyl)propanol.

The 2-bromo-1-bromomethyl-1-(2-fluoro-4-trifluoromethylphenyl)propanol, used as starting material in the above process, may be prepared as follows:

A solution of 1-bromo-2-fluoro-4-trifluoromethylbenzene (5.0 g.) in anhydrous diethyl ether (20 ml.) was added dropwise during 20 minutes to a stirred solution of n-butyl-lithium (19.0 ml.) in anhydrous diethyl ether (25 ml.) at −70°, under an atmosphere of argon. A solution of 1,3-dibromobutan-2-one (5.67 g.) in anhydrous diethyl ether (15 ml.) was added dropwise, and the mixture was stirred for a further ½ hour after completion of the addition. The mixture was allowed to warm to −30°, and a solution of acetic acid (5 ml.) in ether (20 ml.) was added, followed by water (20 ml.), and the reaction mixture was then allowed to warm to room temperature, and stirred for 10 minutes. The aqueous layer was separated and washed with ether, and the washings were combined with the organic layer. The combined organic solutions were washed with water then brine, dried and evaporated to dryness, and the residue was azeotroped twice with toluene to give the required starting material.

EXAMPLE 58–60

The process described in Example 57 was repeated, using 2-bromo-1-bromomethyl-1-(2-fluoro-4-trifluoromethylphenyl)-2-methylpropanol as the starting material, and using 50% v/v ethyl acetate/petroleum ether (b.p. 60°–80°) as the chromatography eluting solvent, to give 1-(2-fluoro-4-trifluoromethylphenyl)-2-methyl-2-(1,2,4-triazol-1-yl)-1-(1,2,4-triazol-ylmethyl)-propanol, m.p. 174°–175°.

The 2-bromo-1-bromomethyl-1-(2-fluoro-4-trifluoromethylphenyl)-2-methylpropanol used as starting material in the above process was manufactured by the process described in the latter part of Example 57, but starting from 1,3-dibromo-3-methylbutan-2-one instead of 1,3-dibromobutan-2-one.

The process described first above was repeated, using the appropriate dibromopropanol derivative, to obtain the following compounds:

EXAMPLE 59

1-(4-chlorophenyl)-2-methyl-2-(1,2,4-triazol-1-ylmethyl)propanol, m.p. 122°–123°.

EXAMPLE 60

1-(2,4-difluorophenyl)-2-methyl-(1,2,4-triazole-1-yl)-1-(1,2,4-triazol-1-ylmethyl)propanol, m.p. 148°–149°.

The required dibromopropanol starting materials were obtained by repeating the process described second above, using the appropriate substituted bromobenzene.

EXAMPLE 61-62

A mixture of 4-chloro-α-(1,2,4-triazol-1-yl)-butyrophenone (2.5 g.), trimethylsulphoxonium iodide (2.64 g.), potassium hydroxide (1.34 g.) and 1,2,4-triazole (0.83 g.) in tert-butyl alcohol (25 ml.) was heated at 70° for 12 hours, then cooled, poured into water and extracted with ethyl acetate. The ethyl acetate extract was separated, washed with water and then brine, dried, and evaporated to dryness under reduced pressure. The residue was purified on a silica column, eluting with 50% v/v ethyl acetate/petroleum ether (b.p. 60°-80°), and crystallised from a mixture of ethyl acetate and hexane to give 1-(4-chlorophenyl)-2-(1,2,4-triazol-1-yl)-1-(1,2,4-triazol-1-ylmethyl)butanol, m.p. 168°-169° (Example 61).

In a similar manner, starting from 2,6-difluoro-α-(1,2,4-triazol-1-yl)butyrophenone, there was obtained 1-(2,6-difluorophenyl)-2-(1,2,4-triazol-1-yl)-1-(1,2,4-triazol-1-ylmethyl)butanol, m.p. 110°-111° (Example 62).

The 4-chloro-α-(1,2,4-triazol-1-yl)butyrophenone, used as starting material in the above process, was obtained as follows:

Bromine (10 g.) was added dropwise to a stirred solution of 4-chlorobutyrophenone (9.7 g.) in dichloromethane (25 ml.), and the mixture was stirred for a further 15 minutes, then evaporated to dryness under reduced pressure. The residue was dissolved in ethyl acetate, and the solution was washed twice with water then with brine, dried and evaporated to dryness to give α-bromo-4-chlorobutyrophenone as an oil.

The α-bromo-4-chlorobutyrophenone (14.4 g.) was dissolved in dimethylformamide (75 ml.), sodium 1,2,4-triazole (5.5 g.) was added, and the solution was heated at 70° for 2 hours, then poured into water and extracted with ethyl acetate. The extract was washed with water and brine, and evaporated to dryness under reduced pressure. The residue was purified on a silica column, eluting with 50% v/v ethyl acetate/petroleum ether (b.p. 60°-80°), then by crystallisation from ethyl acetate/hexane to give the required butyrophenone starting material.

The starting butyrophenone for Example 62 was obtained similarly, starting from 2,6-difluorobutyrophenone.

EXAMPLES 63-69

The process described in Example 14 was repeated, using the appropriate substituted phenone as starting material, to give the following compounds:

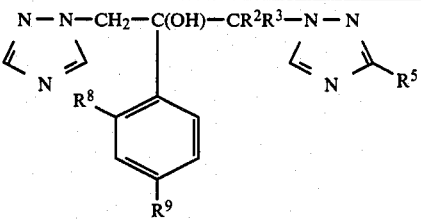

| Ex | $R^2$ | $R^3$ | $R^8$ | $R^9$ | $R^5$ | M.p. |
|---|---|---|---|---|---|---|
| 63 | $CH_3$ | H | F | F | H | 180-181 |
| 64 | $CH_3$ | $CH_3$ | H | F | H | 133-137 |
| 65 | $CH_3$ | H | H | Cl | isobutyl | 140-141 |
| 66 | $CH_3$ | H | H | F | isopropyl | 113-114 |
| 67 | $CH_3$ | H | H | $CF_3$ | 3-pyridyl | 136-137 |
| 68 | $CH_3$ | H | F | F | 3-pyridyl | 165-168 |
| 69 | 2-(1,2,4-triazol-1-yl)-1-(1,2,4-triazol-1-ylmethyl)-1-[3,5-bis(trifluoromethyl)phenyl]propanol, m.p. 177-178° | | | | | |

EXAMPLE 70

The process described in the first part of Example 1 was repeated, using 3-(4-fluorobenzyl)-1,2,4-triazole in place of 3-(4-chlorostyryl)-1,2,4-triazole, and 4-trifluoromethyl-α-(1,2,4-triazol-1-yl)acetophenone in place of the 2,4-dichloro compound, to give 2-(4-fluorobenzyl-1,2,4-triazol-1-yl)-1-(1,2,4-triazol-1-ylmethyl)-1-(trifluoromethylphenyl)ethanol, m.p. 100°-103°.

What we claim is:

1. A compound of the formula:

wherein X and Y are each a nitrilo radical, $R^2$, $R^3$ and $R^4$ are each a hydrogen atom, $R^1$ is a phenyl radical which bears one or two substituents selected from trifluoromethyl and halogen, and $R^5$ is a phenyl or styryl radical similarly substituted.

2. A compound as claimed in claim 1 wherein $R^1$ is a 4-trifluoromethyl-, 2,4-difluoro-, 2,4-dichloro- or 2-fluoro-4-trifluoromethyl-phenyl radical, and $R^5$ is a 4-trifluoromethyl-, 4-fluoro-, 2,4-difluoro- or 4-chlorophenyl or -styryl radical.

3. A compound of the formula shown in claim 1 wherein X and Y are each a nitrilo radical, $R^2$, $R^3$ and $R^4$ are each a hydrogen atom, $R^1$ is a 4-trifluoromethylphenyl or 2,4-difluorophenyl radical and $R^5$ is a 4-trifluoromethylphenyl, 4-trifluoromethylstyryl, 4-fluorophenyl, 4-fluorostyryl, 2,4-difluorophenyl or 2,4-difluorostyryl radical.

* * * * *